(12) United States Patent
Jackson et al.

(10) Patent No.: US 11,491,214 B2
(45) Date of Patent: Nov. 8, 2022

(54) TREATMENT OF ABNORMAL CUTANEOUS SCARRING

(71) Applicant: ZZ Biotech LLC, Houston, TX (US)

(72) Inventors: Christopher John Jackson, New South Wales (AU); Meilang Xue, New South Wales (AU)

(73) Assignee: ZZ BIOTECH LLC, Houston, TX (US)

( * ) Notice: Subject to any disclaimer, the term of this patent is extended or adjusted under 35 U.S.C. 154(b) by 0 days.

(21) Appl. No.: 16/710,387

(22) Filed: Dec. 11, 2019

(65) Prior Publication Data

US 2020/0108128 A1 Apr. 9, 2020

Related U.S. Application Data (63) Continuation of application No. 16/155,475, filed on Oct. 9, 2018, now abandoned, which is a continuation of application No. 15/304,446, filed as application No. PCT/AU2014/050323 on Oct. 29, 2014, now abandoned.

(30) Foreign Application Priority Data

Apr. 16, 2014 (AU) ................................ 2014901397

(51) Int. Cl.
*A61K 38/48* (2006.01)

(52) U.S. Cl.
CPC .. *A61K 38/4866* (2013.01); *C12Y 304/21069* (2013.01)

(58) Field of Classification Search
None
See application file for complete search history.

(56) References Cited

U.S. PATENT DOCUMENTS

| | | |
|---|---|---|
| 4,775,624 A | 10/1988 | Bang et al. |
| 4,959,318 A | 9/1990 | Foster et al. |
| 4,981,952 A | 1/1991 | Yan |
| 5,084,274 A | 1/1992 | Griffin et al. |
| 5,093,117 A | 3/1992 | Lawrence et al. |
| 5,151,268 A | 9/1992 | Bang et al. |
| 5,453,373 A | 9/1995 | Gerlitz et al. |
| 5,516,650 A | 5/1996 | Foster et al. |
| 5,571,786 A | 11/1996 | Eibl et al. |
| 5,831,025 A | 11/1998 | Ogata et al. |
| 6,037,322 A | 3/2000 | Grinnell et al. |
| 6,156,734 A | 12/2000 | Grinnell et al. |
| 6,159,468 A | 12/2000 | Carlson et al. |
| 6,268,344 B1 | 7/2001 | Grinnell et al. |
| 6,395,270 B1 | 5/2002 | Carlson et al. |
| 2007/0224150 A1 | 9/2007 | Chung |
| 2011/0129546 A1 | 6/2011 | Umbert Mill |

FOREIGN PATENT DOCUMENTS

| | | |
|---|---|---|
| AU | 658881 | 11/1992 |
| CA | 2041380 C | 10/1997 |
| CN | 101912450 | 12/2010 |
| EP | 2157176 | 2/2010 |
| WO | 1989/012685 | 12/1989 |
| WO | 93/09807 | 5/1993 |
| WO | 95/29148 | 11/1995 |
| WO | 95/30429 | 11/1995 |
| WO | 98/48818 | 11/1998 |
| WO | 01/56532 | 8/2001 |
| WO | 01/59084 | 8/2001 |
| WO | 2001/072328 | 10/2001 |
| WO | 02/32461 | 4/2002 |
| WO | WO 02/32461 * | 4/2002 |
| WO | 2002/100445 | 12/2002 |
| WO | 2004/041296 | 5/2004 |
| WO | 2005/007820 | 1/2005 |
| WO | 2006136963 A2 | 12/2006 |
| WO | 2008/026014 | 3/2008 |
| WO | 2008/055145 | 5/2008 |
| WO | 2008/073603 | 6/2008 |
| WO | 2009074797 A1 | 6/2009 |
| WO | 2014/005183 | 1/2014 |
| WO | WO 2014/005183 * | 1/2014 |
| WO | 2015/157822 | 10/2015 |

OTHER PUBLICATIONS

Machesney et al. (American Journal of Pathology, vol. 152, No. 5, May 1998) (Year: 1998).*
Kur-Piotrowska et al. (BMC Genomics (2017) 18:56) (Year: 2017).*
Mosnier et al. (Blood, Apr. 15, 2007;109(8):3161-72) (Year: 2007).*
English Translation of Office Action corresponding to Chinese Patent Application No. 201480078924.1 (11 pages) (dated Oct. 8, 2019).
Freedberg et al. "Keratins and the Keratinocyte Activation Cycle" The Journal of Investigative Dermatology, 116(5):633-640 (2001).
Mosnier et al. "Activated protein C variants with normal cytoprotective but reduced anticoagulant activity" Blood, 104(6):1740-1744 (2004).
Abdou et al. "Immunohistochemical Expression of TGF-β1 in Keloids and Hypertrophic Scars" American Journal of Dermatopathology 33(1):84-91 (2011).
Al-Khawajah, Marwan M. "Failure of Interferon-Alpha 2B in the Treatment of Mature Keloids" International Journal of Dermatology 35(7):515-517 (1996).
Altschul et al. "Gapped BLAST and PSI-BLAST: a new generation of protein database search programs" Nucleic Acids Research 25(17):3389-3402 (1997).
Berth-Jones et al. "Vitamin D analogues and psoriasis" British Journal of Dermatology 127:71-78 (1992).
Bettinger et al. "The Effect of TGF-β on Keloid Fibroblast Proliferation and Collagen Synthesis" Plastic and Reconstructive Surgery 98(5):827-833 (1996).
Bush et al. "Therapies with Emerging Evidence of Efficacy: Avotermin for the Improvement of Scarring" Dermatology and Research Practice 2010:1-6 (2010).

(Continued)

*Primary Examiner* — Sergio Coffa
(74) *Attorney, Agent, or Firm* — Myers Bigel, P.A.

(57) ABSTRACT

The invention relates to the prevention and treatment of pathologic scars using APC or analogue thereof.

9 Claims, 3 Drawing Sheets

Specification includes a Sequence Listing.

(56) References Cited

OTHER PUBLICATIONS

Chalmers, Richard L "The evidence for the role of transforming growth factor-beta in the formation of abnormal scarring" International Wound Journal 8:218-223 (2011).
Chiricozzi et al. "Integrative Responses to IL-17 and TNF-a in Human Keratinocytes Account for Key Inflammatory Pathogenic Circuits in Psoriasis" Journal of Investigative Dermatology 131:677-687 (2011.
Cordeiro et al. "Novel antisense oligonucleotides targeting TGF-β inhibit in vivo scarring and improve surgical outcome" Gene Therapy 10:59-71 (2003).
Esmon, Charles T. "Crosstalk between inflammation and thrombosis" Maturitas 47:305-314 (2004).
Esmon, Charles T. "Structure and functions of the endothelial cell protein C receptor" Critical Care Medicine 32 [Suppl.]:S298-S301 (2004).
Feistritzer et al. "Endothelial barrier protection by activated protein C through PAR1-dependent sphingosine 1-phosphate receptor-1 crossactivation" Blood 105:3178-3184 (2005).
Ferguson et al. "Scar-free healing: from embryonic mechanisms to adult therapeutic intervention" Philosophical Transactions of the Royal Society B: Biological Sciences 359(1445):839-850 (2004).
Finigan et al. "Activated Protein C Mediates Novel Lung Endothelial Barrier Enhancement" The Journal of Biological Chemistry 280(17):17286-17293 (2005).
Guo et al. "Neuroprotective activities of activated protein C mutant with reduced anticoagulant activity" European Journal of Neuroscience 29:1119-1130 (2009).
Herrier, RN "Advances in the treatment of moderate-to-severe plaque psoriasis" American Journal of Health-System Pharmacy 68(9)795-806 (2011) (Abstract Only).
Honardoust et al. "Reduced Decorin, Fibromodulin, and Transforming Growth Factor-β3 in Deep Dermis Leads to Hypertrophic Scarring" Journal of Burn Care & Research 33(2):218-227 (2012).
International Search Report and Written Opinion of the International Searching Authority corresponding to International Patent Application No. PCT/AU2014/050323 (9 pages) (dated Dec. 23, 2014).
Jackson et al. "Activated protein C prevents inflammation yet stimulates angiogenesis to promote cutaneous wound healing" Wound Repair and Regeneration 13(3):284-294 (2005).
Kerschen et al. "Endotoxemia and sepsis mortality reduction by non-anticoagulant-activated protein C" The Journal of Experimental Medicine 204(10):2439-2448 (2007).
Kur-Piotrowska et al. "Neotenic phenomenon in gene expression in the skin of Foxn1-deficient (nude) mice—a projection for regenerative skin wound healing" BMC Genomics 18(56):1-15 (2017).
Kurian et al. "Current Effective Topical Therapies in the Management of Psoriasis" Skin Therapy Letter 16(1):4-7 (2011).
Lay et al. "Acute inflammation is exacerbated in mice genetically predisposed to a severe protein C deficiency" Blood 109:1984-1991 (2007).
Le et al. "Transforming Growth Factor Beta 3 is Required for Excisional Wound Repair In Vivo" PloSOne (2012) 7(10).
Ledon et al. "Intralesional Treatment for Keloids and Hypertrophic Scars: A Review" Dermatologic Surgery 39(12):1745-1757 (2013).
Lee et al. "Expression of Transforming Growth Factor Beta 1, 2, and 3 Proteins in Keloids" Annals of Plastic Surgery 43(2):179-184 (1999).
Lin et al. "Exogenous Transforming Growth Factor-Beta Amplifies Its Own Expression and Induces Scar Formation in a Model of Human Fetal Skin Repair" Annals of Plastic Surgery 222(2):146-154 (1995).
Machesney et al. "Activated keratinocytes in the epidermis of hypertrophic scars" Am J Pathol 152(5):1133-41 (May 1998).
Matsumoto et al. "Activated protein C modulates the proinflammatory activity of dendritic cells" Journal of Asthma and Allergy 8:29-37 (2015).

McCollum et al. "Randomized phase II clinical trial of avotermin versus placebo for scar improvement" British Journal of Surgery 98(7):925-934 (2011).
McCoy et al. "In Vitro Inhibition of Cell Growth, Collagen Synthesis, and Prolyl Hydroxylase Activity by Triamcinolone Acetonide" Proceedings of the Society for Experimental Biology and Medicine 163(2):216-222 (1980).
McKelvey et al. "Activated protein C: A regulator of human skin epidermal keratinocyte function" World Journal of Biological Chemistry 5(2):169-179 (2014).
Momtazi et al. "A nude mouse model of hypertrophic scar shows morphologic and histologic characteristics of humar hypertrophic scar" Wound Repair and Regeneration 21(1):77-87 (2013).
Montesu et al. "Adverse reactions during biological drug therapy in psoriasis: clinical series and a review of the literature" G. Ital. Dermatol. Venereol. 146(4):273-281 (2011) (Abstract Only).
Mosnier et al. "Protein C anticoagulant activity in relation to anti-inflammatory and anti-apoptotic activities" Frontiers in Bioscience 11:2381-2399 (2006).
Nestle et al. "Skin immune sentinels in health and disease" Nature Reviews Immunology 9(10):679-691 (2009).
O'Brien et al. "Activated Protein C Decreases Tumor Necrosis Factor-Related Apoptosis-Inducing Ligand by an EPCR-Independent Mechanism Involving Egr-1/Erk-1/2 Activation" Arteriosclerosis, Thrombosis, and Vascular Biology 27(12):2634-2641 (2007).
Occleston et al. "Prevention and reduction of scarring in the skin by Transforming Growth Factor beta 3 (TGFβ3): from laboratory discovery to clinical pharmaceutical" Journal of Biomaterials Science, Polymer Edition 19(8):1047-1063 (2008).
Pasparakis, Manolis "Regulation of tissue homeostasis by NF-?B signalling: implications for inflammatory diseases" Nature Reviews Immunology 9:778-788 (2009).
Pasparakis, Manolis "Role of NF—?B in epithelial biology" Immunological Reviews 246:346-358 (2012).
Pearson, William R. "Searching Protein Sequence Libraries: Comparison of the Sensitivity and Selectivity of the Smith-Waterman and FASTA Algorithms" Genomics 11(3):635-650 (1991).
Profyris et al. "Cutaneous scarring: Pathophysiology, molecular mechanisms, and scar reduction therapeutics Part I. The molecular basis of scar formation" Journal of the American Academy of Dermatology 66(1):1-10 (2012).
Russian Office Action corresponding to Russian Patent Application No. 2015103510 (12 pages) (dated Dec. 8, 2017).
Shah et al. "Neutralising antibody to TGF-β1,2 reduces cutaneous scarring in adult rodents" Journal of Cell Science 107:1137-1157 (1994).
Skripin, Y.K. "Skin and Venereal Diseases" M, Triada-X, p. 363 (2000) (Concise Statement).
Smith et al. "Identification of Common Molecular Subsequences" Journal of Molecular Biology 147(1):195-197 (1981).
Thompson et al. "Genetic Risk Factors for Hypertrophic Scar Development" Journal of Burn Care & Research 34(5):477-482 (2013).
Tran et al. "Insight into psoriasis management: Commercial perspectives for the U.S. psoriasis market" Journal of Dermatological Treatment 22:18-26 (2011).
Uchiba et al. "Activated Protein C Induces Endothelial Cell Proliferation by Mitogen-Activated Protein Kinase Activation In Vitro and Angiogenesis In Vivo" Circulation Research 95:34-41 (2004).
Van Zonneveld et al. "Inflammation, vascular injury and repair in rheumatoid arthritis" Annals of the Rheumatic Diseases 69(Suppl. 1):i57-i60 (2010).
Vetrano et al. "Unexpected role of anticoagulant protein C in controlling epithelial barrier integrity and intestinal inflammation" Proceedings of the National Academy of Sciences 108(49):19830-19835 (2011).
Walker et al. "Activated protein C analog with reduced anticoagulant activity improves functional recovery and reduces bleeding risk following controlled cortical impact" Brain Research 1347:125-131 (2010).

(56) References Cited

OTHER PUBLICATIONS

Wallis, Robert S. "Biologics and Infections: Lessons from Tumor Necrosis Factor Blocking Agents" Infectious Disease Clinics of North America 25(4):895-910 (2011).

Wang et al. "An Activated Protein C Analog With Reduced Anticoagulant Activity Extends the Therapeutic Window of Tissue Plasminogen Activator for Ischemic Stroke in Rodents" Stroke 43(9):2444-2449 (2012).

White et al. "Activated protein C inhibits lipopolysaccharide-induced nuclear translocation of nuclear factor ?B (NF-?B) and tumour necrosis factor a (TNF-a) production in the THP-1 monocytic cell line" British Journal of Haematology 110:130-134 (2000).

Williams et al. "Preclinical Safety and Pharmacokinetic Profile of 3K3A-APC, a Novel, Modified Activated Protein C for Ischemic Stroke" Current Pharmaceutical Design 18(27):4215-4222 (2012).

Xia et al. "Complex epithelial-mesenchymal interactions modulate transforming growth factor-β expression in keloid-derived cells" Wound Repair and Regeneration 12(5):546-556 (2004).

Xu et al. "Comparison of the mechanisms of intralesional steroid, interferon or verapamil injection in the treatment of proliferative scars" Zhonghua zhengxing waike zazhi 25(1):37-40 (2009) (Abstract Only).

Xue et al. "Activated Protein C Enhances Human Keratinocyte Barrier Integrity via Sequential Activation of Epidermal Growth Factor Receptor and Tie2" The Journal of Biological Chemistry 286(8):6742-6750 (2011).

Xue et al. "Activated protein C stimulates proliferation, migration and wound closure, inhibits apoptosis and upregulates MMP-2 activity in cultured human Keratinocytes" Experimental Cell Research 299:119-127 (2004).

Xue et al. "Differential Regulation of Matrix Metalloproteinase 2 and Matrix Metalloproteinase 9 by Activated Protein C" Arthritis & Rheumatism 56(9):2864-2874 (2007).

Xue et al. "Endothelial Protein C Receptor and Protease-Activated Receptor-1 Mediate Induction of a Wound-Healing Phenotype in Human Keratinocytes by Activated Protein C" Journal of Investigative Dermatology 125:1279-1285 (2005).

Xue et al. "Endothelial protein C receptor is Overexpressed in rheumatoid arthritic (RA) synovium and mediates the anti-inflammatory effects of activated protein C in RA monocytes" Annals of the Rheumatic Diseases 66:1574-1580 (2007).

Xue et al. "Protein C Is an Autocrine Growth Factor for Human Skin Keratinocytes" The Journal of Biological Chemistry 282(18):13610-13616 (2007).

Yuksel et al. "Activated Protein C Inhibits Lipopolysaccharide-Induced Tumor Necrosis Factor-a Production by Inhibiting Activation of both Nuclear Factor-?B and Activator Protein-1 in Human Monocytes" Thrombosis and Haemostasis 88:267-273 (2002).

Zaba et al. "Identification of TNF-related apoptosis-inducing ligand and other molecules that distinguish inflammatory from resident dendritic cells in patients with psoriasis" Journal of Allergy and Clinical Immunology 125(6):1261-1268 (2010).

Zanni, Guido "Psoriasis: issues far more serious than cosmetic" The Consultant Pharmacist 27(2):86-88, 90, 93-86 (2012) (Abstract Only).

Andriessen et al. "Hypertrophic Scarring is Associated With Epidermal Abnormalities: An Immunohistochemical Study" Journal of Pathology, 186(2):192-200 (1998).

Jiang et al. "Epidermal growth factor and transforming growth factor alpha specifically induce the activation- and hyperproliferation-associated keratins 6 and 16" Proceedings of the National Academy of Sciences of the United States of America, 90(14):6786-6790 (1993).

Julovi et al. "Protease Activated Receptor-2 Mediates Activated Protein C-Induced Cutaneous Wound Healing via Inhibition of p38" The American Journal of Pathology, 179(5):2233-2242 (2011).

Bae et al. "Thrombin Down-Regulates the TGF-β-Mediated Synthesis of Collagen and Fibronectin by Human Proximal Tubule Epithelial Cells Through the EPCR-Dependent Activation of PAR-1" Journal of Cellular Physiology, 225:233-239 (2010).

Guo et al. "An Activated Protein C Analog Stimulates Neuronal Production by Human Neural Progenitor Cells via a PAR1-PAR3-S1PR1-Akt Pathway" The Journal of Neuroscience, 33(14):6181-6190 (2013).

Herdrich et al. "Fetal Tendon Wound Size Modulates Wound Gene Expression and Subsequent Wound Phenotype" Wound Repair and Regeneration, 18:543-549 (2010).

Boulaftali et al. "Endothelial Protease Nexin-1 Is a Novel Regulator of A Disintegrin and Metalloproteinase 17 Maturation and Endothelial Protein C Receptor Shedding via Furin Inhibition" Arterioscler Tromb Vac Biol., 33:1647-1654 2013.

Cabrijan et al. "Psoriasis Vulgaris—An Inflammatory Skin Disease and/or Benign Epidermal Hyperplasia" Acta Dermatovenerologica Croatica 19(2):117-119 (2011).

Fukushiro, Torri (1999), Characteristics of cultured cells of human epidermal keratinocytes from hypertrophic scars and of its apoptosis, Proceedings from 13th Conference on Disorders of Keratinisation, p. 58-61.

Kuroda et al. "Altered Expression of Angiopoietins and Tie2 Endothelium Receptor in Psoriasis" Journal of Investigative Dermatology 116:713-720 (2001).

* cited by examiner

3K3A is SEQ ID NO. 1

Figure 3 (SEQ ID No: 1)

ANSFLEELRHSSLERECIEEICDFEEAKEIFQNVDDTLAFWSKHVDGDQCLV
LPLEHPCASLCCGHGTCIDGIGSFSCDCRSGWEGRFCQREVSFLNCSLDNGGCTHYC
LEEVGWRRCSCAPGYKLGDDLLQCHPAVKFPCGRPWKRMEKKRSHLKRDTEDQED
QVDPRLIDGKMTRRGDSPWQVVLLDSAAALACGAVLIHPSWVLTAAHCMDESKKLLV
RLGEYDLRRWEKWELDLDIKEVFVHPNYSKSTTDNDIALLHLAQPATLSQTIVPICLPDS
GLAERELNQAGQETLVTGWGYHSSREKEAKRNRTFVLNFIKIPVVPHNECSEVMSNM
VSENMLCAGILGDRQDACEGDSGGPMVASFHGTWFLVGLVSWGEGCGLLHNYGVYT
KVSRYLDWIHGHIRDKEAPQKSWAP

TREATMENT OF ABNORMAL CUTANEOUS SCARRING

CROSS REFERENCE TO RELATED APPLICATIONS

This application is a continuation of U.S. application Ser. No. 16/155,475, filed Oct. 9, 2018, which is a continuation of U.S. application Ser. No. 15/304,446, filed Oct. 14, 2016, which is a filing under 35 U.S.C. 371 of PCT/AU2014/050323, filed Oct. 29, 2014, which claims priority from Australian Application No. 2014901397, filed Apr. 16, 2014. These prior applications are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9975-10CT2-updated_ST25.txt, 4,367 bytes in size, generated on Apr. 23, 2021 and filed via EFS-Web, is provided in lieu of a paper copy. This Sequence Listing is hereby incorporated by reference into the specification for its disclosures.

FIELD OF THE INVENTION

The invention relates to abnormal cutaneous scarring, including hypertrophic, atrophic and keloid scarring and to treatment of same.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

In the adult, the normal response to injury is generally wound repair, a physiological process that results in some degree of fibrosis, leading to formation of scar tissue. Although perhaps a cosmetic imperfection, it is widely accepted that scar tissue arising from wound repair is in fact a normal tissue formation.

Histologically, scar tissue arising from a normal wound repair process appears as a dense, almost avascular, parvicellular extracellular matrix composed predominantly of collagen type I. The distribution and alignment of type I collagen may be unlike that in the tissue before injury, and in particular scar tissue may have a more pronounced alignment of type I collagen in a single direction as compared with collagen laid down in tissue before injury. Further, there may be more extensive cross linking between collagen fibres in an scar as compared with that observed in tissue before injury.

Physiologic scar formation has been classically described as following three distinct phases consisting of an initial phase in which a fibrin clot is formed, an intermediate phase in which the fibrin clot is lysed and a temporary matrix consisting of proteoglycan, glycoprotein and type III collagen is laid down, and a final phase in which the temporary phase is digested and replaced with a matrix rich in collagen type I.

Local factors, such as the type, size and location of the wound, the vascular supply to the wound, the presence of infection, local movement, and exposure to radiation and UV light influence wound repair and therefore physiologic scar formation. Systemic factors including status of cardiovascular performance, infection, metabolic status and hormones also influence physiologic scar formation.

It is generally accepted that a normal physiological response to injury is a wound repair process that is complete with evidence of collagen type I deposition by about 3 to 4 weeks from injury. A protraction of the wound repair process beyond this time increases the likelihood of formation of a pathologic scar in place of a physiologic scar (Momtazi et al. 2013 Wound Repair and Regeneration 21:77-87).

A pathologic scar may be referred to as a disorder of the skin resulting from dysregulated proliferation or formation of fibrotic tissue. Particular examples include hypertrophic scars, atrophic scars and keloid scars. Pathologic scars are of particular concern because they may cause more significant cosmetic disfigurement, and functional limitations that include pain, pruritus, heat intolerance, reduced range of motion and lifelong disability to contractures.

While there are some clear differences as between hypertrophic scars, atrophic scars and keloid scars, it is generally believed that pathologic scars generally arise from abnormal signalling and proliferation of cells, especially fibroblasts and myofibroblasts.

Further, the balance between TGF-β1 and TGF-β3 is an important regulator of scar formation. The increase or prolonged activity of TGF-β1 leads to an overproduction and excess deposition of collagen by fibroblasts that often results in hypertrophic scars (Abdou et al. 2011 Am J Dermatopathol. 33: 84-91; Honardoust, et al. 2012, J. Burn Care Res. 33: 218-227; Chalmers 2011 Int Wound J 8: 218-223).

Overexpression of TGF-β1 and 32 has been found in keloid and keloid-derived fibroblasts, with significantly lower TGF-β3 mRNA expression (Lee T Y, et al. Ann Plast Surg. 1999; 43:179-84; Xia W, et al. Wound Repair Regen. 2004; 12:546-56). It has been shown that anti-TGF-β1 and β2 antibodies can reduce wound scarring in rat incision wounds (Shah, M. et al, J Cell Sci 107: 1137-57, 1994). Antisense phosphorothioate oligonucleotides against TGF-β1 and β2 have been used in vivo to significantly reduce postoperative scarring in rabbit and mouse models of glaucoma surgery (Cordeiro M F, et al. Gene Ther. 2003; 10:59-71). The addition of TGFβ1 to a rat fetal wound that would normally heal without a scar results in scar formation (Lin R Y, et al. Ann Surg. 1995; 222(2):146-154). Further keloid fibroblasts have been shown to be hypersensitive to TGF-β (Bettinger et al. 1996 Plast Reconstr Surg 98:827-833). Mice embryos that are genetically null for TGFβ3 heal with a scar in comparison with wild-type littermates, which exhibit scar-free healing (Occleston N L, et al. J Biomater Sci Polym Ed. 2008; 19(8):1047-63). In three double-blind, placebo-controlled studies, intradermal human recombinant TGFβ3, avotermin improves the appearance of scars (Bush J, et al. Dermatol Res Pract. 2010; 2010:690613).

The above studies suggest that it is the persistent expression of TGF receptors and/or TGF-β1 and/or lack of TGF-β3 that is associated with protraction of wound repair leading to formation of pathological scar. Further, it is also understood that the expression TGF-β1 is relevant to the persistence of pathological scars that have arisen from a protracted wound repair process. This follows from the fact that many of the modalities utilised in the clinic today for treatment of hypertrophic scars target TGF-β1 itself.

Corticosteroids, methotrexate, interferon α and β and some cytokine inhibitors have been used with some success for treatment of hypertrophic scars and keloids. Corticosteroids are considered to be a criterion standard and are understood to inhibit fibroblast growth and promote collagen degradation (McCoy et al. 1980 Proc Soc Exp Biol Med 163: 216-222.). Triamcinolone is one example of a corticosteroid that has been found to inhibit TGF-βI expression and induce apoptosis in fibroblasts (Xu et al. 2009 Chinese J. Plastic Surg 25:37-40).

Corticosteroid therapy may result in unwanted side effects of scar atrophy, tissue pigmentation and pain. Interferon therapy may result in fever, headache, arthralgia, fatigue, chills and confusion (al Khawajah 1996 Int. J. Dermatol. 35: 515-517), and there is some question as to overall efficacy (Ledon et al. 2013 Dermatol Surg 39:1745-1757.)

Other modalities proposed for the treatment of pathological scars are diverse with respect to chemistry and the mechanism of action that they propose to target. These include botulinum toxin A, pentoxifylline, minocycline, collagen-glycosaminoglycan copolymers, recombinant TGF β3, mannose-6-phosphate, interleukin-10, insulin and propranolol (Ledon supra).

There remains a need to minimise the likelihood of pathologic scar formation, in particular to minimise the likelihood of formation of hypertrophic scars.

There also remains a need to treat pathologic scars such as hypertrophic scars.

SUMMARY OF THE INVENTION

The invention seeks to address one or more limitations of the prior art and provides a method for inducing a skin cell, such as a fibroblast or keratinocyte to express or produce TGF-β3. The invention further provides a method for inhibiting TGF-βI expression or production by a skin cell.

The invention also provides a method for inhibiting or preventing the formation of a pathologic scar, especially a hypertrophic scar. The invention also provides a method for minimising or reducing the appearance of a pathologic scar. These methods of the invention utilise activated protein C (APC) or analogues thereof including APC-3K3A (SEQ ID NO: 1) to induce TGF-β3 production or to inhibit TGF-βI induction, thereby enabling the inhibition of pathogenic scar formation and minimisation of appearance of a pathologic scar.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Activated protein C (APC) is the activated form of Protein C (also known as autoprothrombin IIA and blood coagulation factor XIV) which plays an important role in regulating blood clotting, inflammation, cell death, and maintaining the permeability of blood vessel walls in humans and other animals. APC performs these operations primarily by proteolytically inactivating proteins Factor Va and Factor VIIIa.

As described herein, the inventors have identified that APC and APC 3K3A (SEQ ID NO: 1) each have common influences on the skin cell production of various isoforms of TGF-β. Specifically, the inventors have shown that both APC and APC 3K3A (SEQ ID NO: 1) enhance skin cell TGF-β3 production. Cells that constitutively expressed TGF-β3 were shown to have increased production of TGF-β3 from contact with APC or APC 3K3A (SEQ ID NO: 1) compared with untreated controls. Importantly, the production of TGF-βI was not substantially enhanced in APC or APC-3K3A (SEQ ID NO: 1)-treated skin cells.

It is believed that the large increase in TGF-β3 production or expression (up to 6 fold in respect of APC-3K3A (SEQ ID NO: 1) treated skin cells compared with untreated controls) is important for minimising formation of pathologic scars or for treatment of pathologic scars, irrespective of the amount of TGF-βI production or expression.

Further, the constitutive expression of TGF-βI was inhibited when the APC-enhanced skin cell production of TGF-β3 had ceased. Further, the inhibition of constitutive TGF-βI expression in APC treated skin cells did not inhibit the constitutive expression of TGF-β3.

From the above observations, the inventors have identified the utility of APC and APC-3K3A (SEQ ID NO: 1) in the selective enhancement of constitutive expression or production of TGF-β3 by skin cells, such as fibroblasts, myofibroblasts, keratinocytes and endothelial cells, or composition including one or more of these cells, and the selective inhibition of constitutive expression or production of TGF-βI by skin cells. On the basis of these findings, and the known importance of TGF-βI and TGF-β3 isoforms in wound repair and persistence of pathogenic scars, the inventors have identified APC and APC analogues such as APC-3K3A (SEQ ID NO: 1) as potential modalities for minimising the likelihood of pathologic scar formation and for minimising the appearance of pathologic scars.

A. Definitions

The term "comprise" and variations of the term, such as "comprising", "comprises" and "comprised", are not intended to exclude further additives, components, integers or steps.

A 'normal scar' or 'physiologic scar' is generally a tissue formation arising from a normal wound repair process. Histologically, a normal scar or physiologic scar may appear as a dense, almost avascular, parvicellular extracellular matrix composed predominantly of collagen type I.

"Pathologic scar" generally refers to a scar that arises from abnormal wound repair processing, for example a wound repair process that has been protracted or prolonged leading to a delayed formation of temporary or final matrix, or a failure to produce either matrix. The protracted wound repair process may be one associated with significant or prolonged inflammation. These scars may be distinguished histologically from normal scars by the presence of whorled, hyalinised bundles of collagen and having a greater vascularity and cellularity than a normal scar. A pathologic scar may be a scar that is confined within the boundaries of the injury site, or that extends beyond those boundaries. A pathologic scar may cause a reduced range of motion and lifelong disability to contracture, significant cosmetic disfigurement, and functional limitations that include pain, pruritus, heat intolerance.

"Pathologic scar formation" generally refers to a process by which a pathologic scar is formed. In such a process, at least one of the normal phases of wound repair that would normally lead to formation of temporary or final matrix is disturbed. Such a process may lead to a delayed time to closure of a wound by the pathologic scar. In this sense, the process by which the pathologic scar is formed may represent a protraction or prolonging of a normal wound repair process, although it is understood that the mechanisms of action underpinning a pathologic scar formation are not the same as those underpinning a normal physiological response to injury in the form of wound repair.

"A fibro-proliferative disorder" generally refers to a disorder involving the abnormal proliferation of fibroblasts and fibrocytes, or an abnormal level of activity of fibroblasts and fibrocytes including development of an abnormal cytokine profile by fibroblasts or fibrocytes, leading to formation of excessive fibrotic tissue.

"A hypertrophic scar" is an example of a pathological scar and is a raised scar that remains within the boundaries of the original lesion, generally regressing spontaneously after the initial injury. These scars are hard, raised, red, itch, tender and contracted. These scars are seen after burn injury and they enlarge by pushing on the scar's boundary. A hypertrophic scar may contain fibroblasts that are non-proliferative and a lesser subset that rapidly proliferates and demonstrates active synthesis. Histologically, a hypertrophic scar may present as fine, well-organised, wavy type III collagen bundles oriented parallel to the epidermis surface with abundant nodules containing myofibroblasts and plentiful mucopolysaccharide, with low levels of PCNA (proliferating cell nuclear antigen)/p53-level/ATP expression. A hypertrophic scar may arise within 4 to 8 weeks after injury, enter a rapid growth phase for up to 6 months and then regress over a few years.

A "keloid" or "keloid scar" is a benign fibrous proliferation that extends beyond the boundary of the initial wound or site of injury. They are permanent scars that do not regress. Histologically these scars may present as disorganised, large, thick type I and III hypocellular collagen bundles with no nodules or excess myofibroblasts. They may be poorly vascularized with widely scattered dilated blood vessels. PCNA/p53-level/ATP expression levels may be high.

"Atrophic scar" is a scar arising from an abnormal wound repair process leading to the formation of a depression in skin tissue.

"Fibroblast" is generally a cell of mesodermal origin that produces precursors of the extra cellular matrix. These cells are essential for wound repair.

"Wound bed fibroblast", is a fibroblast that may be isolated from or adjacent a site of injury undergoing normal wound repair.

"Keloid fibroblast" is a fibroblast that may be isolated from, or adjacent, a keloid.

"Hypertrophic scar fibroblast" is a fibroblast that may be isolated from, or adjacent a hypertrophic scar.

"Myofibroblast" generally refers to a cell that is in between a fibroblast and a smooth muscle cell in differentiation. Myofibroblasts usually stain for the intermediate filament vimentin which is a general mesenchymal marker and "alpha smooth muscle actin". They are positive for other smooth markers like another intermediate filament type desmin positive in some tissues but may be negative for desmin in some others. Some stellate form myofibroblasts may also be positive for GFAP.

"Keratinocyte" generally refers to an epidermal cell that synthesizes keratin and other proteins and sterols. These cells constitute 95% of the epidermis, being formed from undifferentiated, or basal, cells at the dermal-epidermal junction. Its characteristic intermediate filament protein is cytokeratin. In its various successive stages, keratin forms the prickle cell layer and the granular cell layer, in which the cells become flattened and slowly die to form the final layer, the stratum corneum, which gradually exfoliates.

"Endothelial cell" generally refers to cells that form the endothelium. The endothelium is the thin layer of cells that lines the interior surface of blood vessels and lymphatic vessels, forming an interface between circulating blood or lymph in the lumen and the rest of the vessel wall.

"Activated protein C" ("APC") is a serine protease having a molecular weight of about 56 kD that plays a central role in physiological anticoagulation. The inactive precursor, protein C, is a vitamin K-dependent glycoprotein synthesised by the liver and endothelium and is found in plasma. Activation of protein C occurs on the endothelial cell surface and is triggered by a complex formed between thrombin and thrombomodulin. Another endothelial specific membrane protein, endothelial protein C receptor (EPCR), has been shown to accelerate this reaction more than 1000-fold.

The 'analogue' in the phrase "APC or an analogue thereof", refers to an "APC analogue". An APC analogue is generally a compound that may act via the endothelial protein C receptor (EPCR) and the protease activated receptor-1 (PAR-1), or the PAR-1 and protease activated receptor-3 (PAR-3), to minimise apoptosis, or to increase cell survival in stressed or injured cells. As described further herein, APC analogues generally have a sequence that is homologous to human protein C sequence.

"Treating" and "treatment" generally refers to the management and care of a patient for the purpose of combating a disease, condition, or disorder whether to eliminate the disease, condition, or disorder, or prophylactically to prevent the onset of the symptoms or complications of the disease, pathological condition, or disorder.

B. APC Induction of TGF-β3 Expression

In certain embodiments there is provided a method for inducing the expression or production of TGF-β3 by a skin cell including the steps of contacting a skin cell with APC or APC-3K3A (SEQ ID NO: 1); thereby inducing the expression or production of TGF-β3 by the skin cell.

In one embodiment, the skin cell constitutively expresses or produces TGF-β3.

In one embodiment, the skin cell constitutively expresses or produces TGF-βI.

The skin cell may be a fibroblast, a myofibroblast, a keratinocyte or an endothelial cell.

Where the skin cell is a fibroblast, it may consist of a wound bed fibroblast, a keloid fibroblast and a hypertrophic scar fibroblast.

Typically the contact of the skin cell with APC or APC-3K3A (SEQ ID NO: 1) enhances the expression or production of the TGF-β3 by the skin cell, for example it increases the expression or production of TGF-β3 by the skin cell so that the expression or production of TGF-β3 by the skin cell is greater than the expression or production of TGF-β3 by the untreated skin cell.

Thus in one embodiment, the invention provides a method for enhancing the constitutive expression or production of TGF-β3 by a skin cell, such as a fibroblast, a myofibroblast, a keratinocyte or an endothelial cell, including the step of contacting a skin cell having constitutive expression or production of TGF-β3 with APC or APC-3K3A (SEQ ID NO: 1), thereby enhancing the constitutive expression or production of TGF-β3 by the skin cell.

Typically the expression or production of TGF-β3 by APC or APC-3K3A (SEQ ID NO: 1) treated skin cells is enhanced by about 100 to 500% in treated fibroblasts, and about 5 to 50% in treated keratinocytes, relative to the constitutive expression or production of TGF-β3 of the skin cells.

Typically the expression or production of TGF-β3 by APC or APC-3K3A (SEQ ID NO: 1) treated skin cells is induced or enhanced for a period of at least 3 to 4 days following initial contact of the skin cell with the APC or APC-3K3A (SEQ ID NO: 1).

Typically the constitutive expression or production of TGF-βI is not enhanced by the contact of the skin cell with APC or APC-3K3A (SEQ ID NO: 1).

Typically the APC or APC-3K3A (SEQ ID NO: 1) does not induce the proliferation of skin cell.

C. APC Inhibition of TGF-b1 Expression

The invention also provides a method for inhibiting the constitutive expression or production of TGF-βI by a skin cell, such as a fibroblast, a myofibroblast, a keratinocyte or an endothelial cell including the step of contacting the skin cell with APC, thereby inhibiting the constitutive expression or production of TGF-βI by the skin cell.

Where the skin cell is a fibroblast, it may be selected from the group consisting of a wound bed fibroblast, a keloid fibroblast and a hypertrophic scar fibroblast.

Typically the expression or production of TGF-βI is inhibited by APC by about 5 to 30%, preferably about 10 to 25%, preferably about 20% relative to the constitutive expression or production of TGF-βI of the skin cells.

Typically the expression or production of TGF-βI is inhibited at least about 3 to 5 days following contact of the skin cell with APC.

Typically the skin cell constitutively expresses or produces TGF-β3.

Typically the constitutive expression or production of TGF-β3 is not inhibited by the contact of the skin cell with APC.

Typically the APC does not induce the proliferation of skin cells.

D. Inhibition of Pathologic Scar Formation

The invention provides a method for inhibiting or preventing the formation of a pathologic scar in an individual including the steps of:
providing an individual having a site of tissue injury undergoing wound repair;
contacting the site of tissue injury with APC or APC-3K3A (SEQ ID NO: 1);
thereby inhibiting or preventing the formation of a pathologic scar in the individual.

The invention also provides a method for inhibiting or preventing protraction of wound repair at a site of injury in an individual including the steps of:
providing an individual having a site of tissue injury undergoing wound repair;
contacting the site of tissue injury with APC or APC-3K3A (SEQ ID NO: 1);
thereby inhibiting or preventing protraction of wound repair at the site of injury in the individual.

In the above described method, the individual may be one at risk for formation of a pathologic scar. In particular, the individual may be one having systemic or local risk factors for protracted wound repair or otherwise for formation of a pathologic scar. Systemic risk factors include systemic infection, metabolic syndrome, diabetes or glucose intolerance, impaired cardiovascular function. The individual may be genetically predisposed to keloid or hypertrophic scar formation. Local risk factors include those pertaining to the injury including the nature of the injury itself (for example, a trauma or burn), abnormal inflammation, repeated physical stress by movement, or exposure to UV radiation.

The invention may include the step of assessing an individual to determine whether the individual or injury site has one or more systemic or local risk factors described above for formation of a pathologic scar or for a protraction of the wound repair process. Typically, the individual is assessed for one or more systemic or local risk factors applicable to formation of a hypertrophic scar.

With respect to burn injury, particular risk factors may include: genetic, especially dark skin eg. American Indian/ Alaskan Native race, facial burns, higher % TBSA, severity of burn (Thompson C M et al, Genetic risk factors for hypertrophic scar development. J Burn Care Res. 2013 September-October; 34(5):477-82).

Other risk factors include age and hormonal influence. Although keloid scars and hypertrophic scars can develop at any age, they tend to develop more readily during and after puberty. Menopause tends to prompt the regression of scarring and pregnancy tends to exacerbate it. Scars from thyroid surgery (thyroidectomy scars) can be problematic due to hormonal changes.

Genetic factors and previous history are also relevant. Specifically, abnormal scarring is 15 times more likely to occur in darker-skinned individuals. Keloid scar formation occurs in areas of high melanocyte concentration and is rarely found on the eyelids, genitalia, soles and palms. Individuals with ginger hair and freckles are also at an increased risk of keloid scars. People with a previous personal history of keloid scarring are more likely to scar again in an abnormal fashion and those with a family history are also at an increased risk.

Scar location and surgery technique are relevant in that scars over or near muscles that are particularly active often spread or become more visible than the scars formed on less active areas. Skin and wound tension during wound repair is also a contributor to increased scarring.

Wound infection increases the risk of abnormal scarring, and separately, a variety of different types of skin injuries can lead to the development of keloid and hypertrophic scarring including surgery, burns and inflammatory skin processes such as acne, psoriasis and chicken pox Where the individual is assessed as having one or more local or systemic risk factors for formation of a pathologic scar or for a protraction of wound repair process, the method may include the further step of selecting the individual for treatment with APC or APC-3K3A (SEQ ID NO: 1) to inhibit or prevent the formation of a pathologic scar in the individual.

Typically the injury is one arising from insult to dermal, cutaneous or skin tissue. The insult may impact on all layers of dermal tissue, for example on stratum basale (stratum germinativum), stratum spinosum, stratum granulosum, stratum lucidum. Examples of particular injury include laceration, abrasion, rupture, burn, contusion, compression.

The injury may be a burn, including a $1^{st}$, $2^{nd}$ or $3^{rd}$ degree burn.

Typically the injury is an acute injury.

Typically the injury is not associated with chronic inflammation.

Typically the injury is not associated with fibrosis.

Typically the injury is not an inflammatory disorder, an allergic disorder, or an idiopathic disorder or disease.

In one particularly preferred embodiment, the individual has one or more risk factors for formation of a hypertrophic scar and the APC is provided in the form of 3K3A (SEQ ID NO: 1) as defined further below.

The APC or APC-3K3A (SEQ ID NO: 1) may be applied to the site of tissue injury before the wound repair process has formed a temporary matrix. In another embodiment the APC or APC-3K3A (SEQ ID NO: 1) may be applied to the site of tissue injury before the wound repair process has formed a final matrix. Typically the APC or APC-3K3A (SEQ ID NO: 1) is applied at about the time of, or shortly after, formation of the temporary matrix.

Typically the individual is treated with APC or APC-3K3A (SEQ ID NO: 1) so as to provide for completion of wound repair within about 3 to 4 weeks of tissue injury.

The scar formed from the treatment generally has features of a physiologic scar including a predominance of collagen type I and a general lack of features that are characteristic of a hypertrophic scar or keloid. These features can be determined by routine histology or gross examination.

Notwithstanding the foregoing, it is understood by those skilled in the art that the dosage amount of the APC or APC-3K3A (SEQ ID NO: 1) will vary with the particular compound or combination of compounds employed, the disease or condition to be treated, the severity of the disease or condition, the type(s) of local administration, the rate of excretion of the compound, the duration of the treatment, the identify of any other drugs being administered to the animal, the age, size and species of the animal, and like factors known in the medical arts. In general, a suitable daily dose of a compound or combination of compounds will be that amount which is the lowest dose effective to produce a therapeutic effect. The dosage amount, dosage form and mode of administration will be determined by an attending physician within the scope of sound medical judgment. Effective dosage amounts, dosage forms, and modes of administration for the various compounds and combination (s) of compounds can be determined empirically and making such determinations is within the skill of the art.

In certain embodiments, it is important that the APC or APC-3K3A (SEQ ID NO: 1) is provided so as to enable contact of APC or APC-3K3A (SEQ ID NO: 1) with skin cells as described herein at the site of tissue injury, as, while not wanting to be bound by hypothesis, it is believed that it is by this contact that the APC or APC-3K3A (SEQ ID NO: 1) provides for minimising risk of pathologic scar formation. Generally, those cells that have been contacted with APC or APC-3K3A (SEQ ID NO: 1) can be recognised by having the following characteristics: increased proliferation and decreased apoptosis; decreased caspase-3; activation of protease-activated receptors 1, 2 or 3; reduced NF-kB activation; reduced activation of signalling molecule, p38; reduced TNF secretion; increased matrix metalloproteinase (MMP)-2 protein and activation; reduced MMP-9; increased sphingoisine-1-phosphate; increased Angiopoietin (Ang)1 and decreased Ang 2; increased Tie2 activation; activation of signalling molecule Akt. Therefore, contact of cells with APC or APC-3K3A (SEQ ID NO: 1), and therefore, therapeutic efficacy of treatment can be established by assessing for these cell phenotypes.

In certain embodiments, a therapeutically effective amount of APC or APC-3K3A (SEQ ID NO: 1) generally provides an for enhancement of the constitutive production or expression of TGF-$\beta$3 and the inhibition of TGF-$\beta$1 constitutive production or expression. This outcome can be assessed by the methods discussed under part B above, thereby establishing whether a therapeutically effective amount of APC has been provided.

In one embodiment, a therapeutically effective amount of APC or APC-3K3A (SEQ ID NO: 1) may prevent or inhibit the formation of a pathologic scar in an individual. This outcome can be assessed by the qualitative or quantitative measures discussed below.

Scar scales have been devised to quantify scar appearance in response to treatment. There are currently at least 5 scar scales that were originally designed to assess subjective parameters in an objective way: The Vancouver Scar Scale (VSS), Manchester Scar Scale (MSS), Patient and Observer Scar Assessment Scale (POSAS), Visual Analog Scale (VAS), and Stony Brook Scar Evaluation Scale (SBSES). These observer-dependent scales consider factors such as scar height or thickness, pliability, surface area, texture, pigmentation, and vascularity. The measurements range across a continuum of values. Thus, the scales are best used to determine change within an individual rather than between individuals.

Several tools have been applied to assess pliability: the pneumatonometer and cutometer are among the most popular. The pneumatonometer uses pressure to objectively measure skin pliability.

The cutometer is a noninvasive suction device that has been applied to the objective and quantitative measurement of skin elasticity. It measures the viscoelasticity of the skin by analysing its vertical deformation in response to negative pressure. It has been used to measure the effects of treatments on burn scars and to assess scar maturation.

The durometer applies a vertically directed indentation load on the scar to measure tissue firmness.

The Chromameter (Minolta, Tokyo, Japan), the DermaSpectrometer (cyberDERM, Inc, Media, Pa., USA), the Mexameter (Courage-Khazaka, Cologne, Germany), and the tristimulus colorimeter are among the most widely applicable devices to measure colour of scars. These devices use spectrophotometric color analysis to calculate erythema and melanin index.

Ultrasound scanners, such as the tissue ultrasound palpation system (TUPS), have been used to quantify scar thickness.

Laser Doppler perfusion imaging is an established technique for the measurement of burn scar perfusion. It aids in early determination of burn depth and subsequent treatment course. Through constructing color-coded maps of tissue micro-perfusion, laser Doppler perfusion imaging offers a non-invasive alternative to burn wound biopsy.

A 3-dimensional optical profiling system (Primos imaging) may be used to generate a high-resolution topographic representation of the scar, thereby characterizing the scar. Alternatively, a noncontact 3-dimensional digitizer may be applied in the study of keloids to measure scar volume and response to treatment.

In another embodiment, the above outcomes are obtained by establishing a local tissue concentration of APC or APC-3K3A (SEQ ID NO: 1) in the region of skin from 0.1 ug to 10 mg, preferably 1 ug to 1 mg of APC or APC-3K3A (SEQ ID NO: 1) per g of skin tissues. This can be determined by taking skin punch biopsies under local anaesthetics from the same site of injury. The amount of APC or APC-3K3A (SEQ ID NO: 1) may then be determined by methods known in the art. In one example, biopsy tissues are minced and lysed on ice. After centrifugation, the clear supernatants are used to measure the PC concentration by ELISA and APC activity by the chromogenic substrate Spectrozyme PCa assay (American Diagnostica). Enzyme activity is determined by measuring the increase in absorbance of the free chromophore generated per unit time at λ450 nm.

In certain embodiments, the therapeutically effective amount of APC or APC-3K3A (SEQ ID NO: 1) is from 0.1 µg to 5000 µg of APC or APC-3K3A (SEQ ID NO: 1) per cm² of the region of skin to which the APC or APC-3K3A (SEQ ID NO: 1) is applied, or from 1 µg to 2000 µg of APC or APC-3K3A (SEQ ID NO: 1) per cm² of the region of skin to which the APC or APC-3K3A (SEQ ID NO: 1) is applied, or from 10 µg to 1000 µg of APC or APC-3K3A (SEQ ID NO: 1) per cm² of the region of skin to which the APC or APC-3K3A (SEQ ID NO: 1) is applied, or from 10 µg to 500 µg of APC or APC-3K3A (SEQ ID NO: 1) per cm² of the region of skin to which the APC or APC-3K3A (SEQ ID NO: 1) is applied The APC or APC-3K3A (SEQ ID NO: 1) may be administered once per week up to twice daily, depending on the nature of the tissue injury. It is generally provided for no more than 20 weeks of consecutive days, or from no more than 6 weeks of consecutive days.

In certain embodiments, the APC or APC-3K3A (SEQ ID NO: 1) may be administered every 4 to 5 days.

D.1 Topical Application

Topical treatment methods, for example, using a paste, gel, cream, oil, lotion, foam, ointment or like substance are particularly useful where the relevant skin region is one that contains a ruptured skin surface, as this permits penetration of the APC or APC-3K3A (SEQ ID NO: 1) may be administered to the relevant strata of the skin tissue where the fibroblasts reside.

In one embodiment, the therapeutically effective amount of APC or APC-3K3A (SEQ ID NO: 1) may be from 0.1 to 2000 µg, preferably from 10 to 1000 µg of APC or APC-3K3A (SEQ ID NO: 1) per cm² of the region of skin. A higher amount is generally preferred where the skin is more severely affected, or where the individual is at particular risk because of presence of local or systemic factors to pathologic scar formation, as described above. Lower amounts may be preferred where the skin is not severely affected.

The concentration of APC or APC-3K3A (SEQ ID NO: 1) in the formulation may be between about 100 ug/ml and 5 mg/ml. In this embodiment, the volume of composition applied to the skin region may be about 100 ul to 5 ml.

The composition may be provided to the skin generally with a sterile surface, such as a finger or spatula in a layer of no more than about 10 mm thickness, preferably about 3 mm thickness. It may then be rubbed or massaged into the skin region and surrounding area. The application is generally from once per day to once per week, and generally no longer than 20 weeks, or no longer than 12 weeks.

In one embodiment, the APC or APC-3K3A (SEQ ID NO: 1) containing composition may be applied to a solid substrate i.e. a bandage, dressing or the like, and the substrate then fixed to the relevant skin region.

D.2 Intradermal Injection Application

In certain embodiments, the above outcomes are obtained by establishing a local concentration of APC or APC-3K3A (SEQ ID NO: 1) at least 2 times higher than basal line. This amount of APC or APC-3K3A (SEQ ID NO: 1) can be measured by measuring APC or APC-3K3A (SEQ ID NO: 1) activity of skin biopsy using ELISA and chromogenic substrate Spectrozyme PCa assay as mentioned above. Intradermal or subcutaneous injection is generally preferred as an administration route when the stratum corneum is intact and of such nature that there is limited penetration of APC or APC-3K3A (SEQ ID NO: 1) across the skin layer. Generally a fine gauge needle on a (~28-34G) needle on a 1 ml syringe may be used. Multiple injections may be given to cover the surface area of the skin, with ~1 injection per cm². The amount per injection will vary from 10 µl to 1 ml, with typical amount being 50 µl. Generally the administration is given from once per day to once per week, and generally no longer than 20 weeks. Intradermal or sub cutaneous injection can be used concurrently with topical application of APC or APC-3K3A (SEQ ID NO: 1).

E. Treatment of Pathologic Scar

The invention provides a method for minimising or reducing the appearance of a pathologic scar in an individual including the steps of:
providing an individual having a pathologic scar;
contacting the pathologic scar with APC or APC-3K3A (SEQ ID NO: 1);
thereby reducing the appearance of a pathologic scar in the individual.

The treatment may reduce the volume of the scar for example by reducing the depth that the scar extends into the adjacent tissue, or reducing the surface area of tissue covered by the scar.

In one embodiment, the method may result in partial or complete regression of the scar.

The method may result in reduction in pigmentation, in particular in reduction of dark or red pigmentation so as to form a scar that has a skin pigmentation more closely resembling normal skin.

In one embodiment the method involves reducing pain arising from a pathologic scar, for example by reducing the supply of nervous tissue to the scar, or by improving the flexibility of the scar thereby reducing constriction of movement. The latter embodiments may involving reducing tissue contraction by the scar.

The method may result in reducing the cellularity and or vascularity of the pathological scar, or in increasing the constitutive expression or production of TGF-β3 or decreasing or inhibiting the constitutive expression or reduction of TGF-β1 in or adjacent the pathological scar.

The pathological scar may arise from any one of the following injuries to dermal tissue including laceration, abrasion, rupture, burn, contusion, compression.

The injury may be a burn, including a $1^{st}$, $2^{nd}$ or $3^{rd}$ degree burn.

The pathological scar may be a hypertrophic scar, a keloid scar or an atrophic scar.

In one particularly preferred embodiment, the pathological scar is a hypertrophic scar arising from a burn injury and the APC or analogue thereof is 3K3A (SEQ ID NO: 1) (as defined further below).

In certain embodiments, it is important that the APC or APC-3K3A (SEQ ID NO: 1) is provided so as to enable contact of APC or APC-3K3A (SEQ ID NO: 1) with skin cells as referred to herein at the site of the pathologic scar as, while not wanting to be bound by hypothesis, it is believed that it is by this contact that the APC or APC-3K3A (SEQ ID NO: 1) provides for treatment of a pathologic scar. Generally, those cells that have been contacted with APC or APC-3K3A (SEQ ID NO: 1) can be recognised by having the following characteristics: increased proliferation and decreased apoptosis; decreased caspase-3; activation of protease-activated receptors 1, 2 or 3; reduced NF-kB activation; reduced activation of signalling molecule, p38; reduced TNF secretion; increased matrix metalloproteinase (MMP)-2 protein and activation; reduced MMP-9; increased sphingoisine-1-phosphate; increased Angiopoietin (Ang)1 and decreased Ang 2; increased Tie2 activation; activation of signalling molecule Akt. and so contact of cells with APC, and therefore, therapeutic efficacy of treatment can be established by assessing for these cell phenotypes.

In certain embodiments, a therapeutically effective amount of APC or APC-3K3A (SEQ ID NO: 1) generally provides for enhancement of the constitutive production or expression of TGF-$\beta$3 and the inhibition of TGF-$\beta$1 constitutive production or expression. This outcome can be assessed by the methods discussed under part B above, thereby establishing whether a therapeutically effective amount of APC or APC-3K3A (SEQ ID NO: 1) has been provided.

In another embodiment, the above outcomes are obtained by establishing a local tissue concentration of APC in the region of skin from 0.1 ug to 10 mg, preferably 1 ug to 1 mg of APC or APC-3K3A (SEQ ID NO: 1) per g of skin tissues. This can be determined by taking skin punch biopsies under local anaesthetics from the same site of pathologic scar. The amount of APC may then be determined by methods known in the art. In one example, biopsy tissues are minced and lysed on ice. After centrifugation, the clear supernatants are used to measure the PC concentration by ELISA and APC activity by the chromogenic substrate Spectrozyme PCa assay (American Diagnostica). Enzyme activity is determined by measuring the increase in absorbance of the free chromophore generated per unit time at $\lambda$450 nm.

In certain embodiments, the therapeutically effective amount of APC or APC-3K3A (SEQ ID NO: 1) is from 0.1 µg to 5000 µg of APC or APC-3K3A (SEQ ID NO: 1) per cm$^2$ of the region of skin to which the APC or APC-3K3A is applied, or from 1 µg to 2000 µg of APC or APC-3K3A (SEQ ID NO: 1) per cm$^2$ of the region of skin to which the APC or APC-3K3A (SEQ ID NO: 1) is applied, or from 10 µg to 1000 µg of APC or APC-3K3A (SEQ ID NO: 1) per cm$^2$ of the region of skin to which the APC or APC-3K3A (SEQ ID NO: 1) is applied, or from 10 µg to 500 µg of APC or APC-3K3A (SEQ ID NO: 1) per cm$^2$ of the region of skin to which the APC or APC-3K3A (SEQ ID NO: 1) is applied.

The APC or APC-3K3A (SEQ ID NO: 1) may be administered once per week up to twice daily, depending on the nature of the tissue injury. It is generally provided for no more than 20 weeks of consecutive days, or from no more than 6 weeks of consecutive days.

In certain embodiments, the APC or APC-3K3A (SEQ ID NO: 1) may be administered every 4 to 5 days.

E.1 Intralesional Injection

In certain embodiments, the above outcomes are obtained by establishing a local concentration of APC or APC-3K3A (SEQ ID NO: 1) may be administered at least 2 times higher than basal line. This amount of APC or APC-3K3A (SEQ ID NO: 1) may be administered can be measured by measuring APC or APC-3K3A (SEQ ID NO: 1) activity of skin biopsy using ELISA and chromogenic substrate Spectrozyme PCa assay as mentioned above. Intradermal or subcutaneous injection is generally preferred as an administration route for treatment of pathological scars as in these circumstances, the stratum corneum is intact and of such nature that there is limited penetration of APC or APC-3K3A (SEQ ID NO: 1) across the skin layer. Generally a fine gauge needle on a (~28-34G) needle on a 1 ml syringe may be used. Multiple injections may be given to cover the surface area of the skin, with ~1 injection per cm$^2$. The amount per injection will vary from 10 µl to 1 ml, with typical amount being 50 µl. Generally the administration is given from once per day to once per week, and generally no longer than 20 weeks. Intradermal or sub cutaneous injection can be used concurrently with topical application of APC or APC-3K3A (SEQ ID NO: 1).

F. APC & Formulations Thereof

APC or APC-3K3A (SEQ ID NO: 1) for use in a method described above may take the form of a composition, or otherwise be obtained by a process, as described below.

APC may be prepared by in vitro activation of protein C purified from plasma or prepared by recombinant DNA techniques by methods well known in the art. See, e.g., U.S. Pat. Nos. 4,981,952, 5,151,268, 5,831,025, 6,156,734, 6,268,344, and 6,395,270.

Alternatively, APC may be prepared directly by recombinant DNA techniques. See, e.g., U.S. Pat. Nos. 4,981,952, 5,151,268, 6,156,734, 6,268,344 and 6,395,270. Recombinant activated protein C may be produced by activating recombinant human protein C zymogen in vitro or by direct secretion from cells of the activated form of protein C. Protein C may be produced in transgenic animals, transgenic plants, or a variety of eukaryotic cells, including, for example, secretion from human kidney 293 cells as a zymogen then purified and activated by techniques known to the skilled artisan.

APC may be from any species of animal, but human APC is preferred.

Fragments and derivatives of APC may be used in the practice of the invention, provided that they exhibit the activities described herein. See, e.g., U.S. Pat. Nos. 5,151,268, 5,453,373 and 5,516,650 and PCT applications WO 89/12685, WO 01/56532, WO 01/59084, and WO 01/72328.

APC may be a derivative of human APC having proteolytic, amidolytic, esterolytic, and biological (anticoagulant, anti-inflammatory, or pro-fibrinolytic) activities characteristic of human APC. Examples of protein C derivatives are described by Gerlitz, et al., U.S. Pat. No. 5,453,373, and Foster, et al., U.S. Pat. No. 5,516,650, the entire teachings of which are hereby incorporated by reference.

Recombinant APC or protein C may incorporate modifications (eg amino acid substitutions, deletions, and additions of heterologous amino acid sequences), thereby forming APC analogues which may, for example, enhance biological activity or expression of the respective protein. One example is 3K3A-APC (SEQ ID NO: 1) by ZZ Biotech which is a genetically engineered variant of the APC and which has reduced anti-coagulant activity. Specifically, 3K3A-APC (SEQ ID NO: 1) has KKK191/193AAA mutation. This mutation may correspond to loop 37 of APC. Another example of an APC analogue contains the RR229/230AA mutation corresponding to the calcium loop of APC. Another example of an APC analogue contains the RR306/312AA mutation corresponding to the autolysis loop of APC. Another APC analogue contains RKRR306/314AAAA (SEQ ID NO: 2 and SEQ ID NO: 3, respectively) corresponding to the autolysis loop of APC. Each of these examples of APC analogues have reduced anticoagulant activity as compared with activity of native APC. However, each of them has related APC function in terms of binding to EPCR and PAR-1 or PAR-3.

Figure 3:
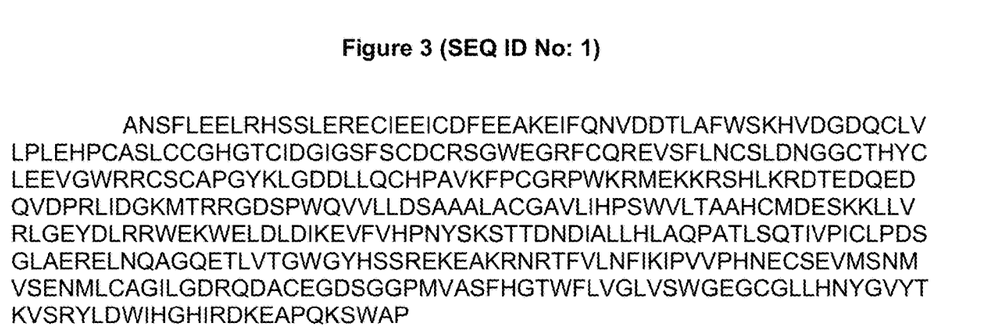
FIG. 3: Amino acid sequence of APC-3K3A (SEQ ID NO: 1).

In a preferred embodiment, the methods of the invention utilise the 3K3A-APC (SEQ ID NO: 1) analogue (KKK191/193AAA) for the various applications described herein including for enhancing the constitutive expression or production of TGF-$\beta$3, or for inhibiting the constitutive expression or production of TGF-$\beta$1, or for minimising the risk of pathologic scar formation, or for reducing the appearance of a pathologic scar. The amino acid sequence of 3K3A-APC (SEQ ID NO: 1) is shown in SEQ ID No: 1.

APC analogues generally have a sequence that is homologous to human protein C sequence. Percentage identity between a pair of sequences may be calculated by the algorithm implemented in the BESTFIT computer program (Smith & Waterman. J. Mol. Biol. 147:195-197, 1981; Pearson, Genomics 11:635-650, 1991). Another algorithm that calculates sequence divergence has been adapted for rapid database searching and implemented in the BLAST computer program (Altschul et al., Nucl. Acids Res. 25:3389-3402, 1997). In comparison to the human sequence, the protein C polynucleotide or polypeptide may be only about 60% identical at the amino acid level, 70% or more identical, 80% or more identical, 90% or more identical, 95% or more identical, 97% or more identical, or greater than 99% identical.

Conservative amino acid substitutions (e.g., Glu/Asp, Val/Ile, Ser/Thr, Arg/Lys, Gln/Asn) may also be considered when making comparisons because the chemical similarity of these pairs of amino acid residues are expected to result in functional equivalency in many cases. Amino acid substitutions that are expected to conserve the biological function of the polypeptide would conserve chemical attributes of the substituted amino acid residues such as hydrophobicity, hydrophilicity, side-chain charge, or size. In comparison to the human sequence, the protein C polypeptide may be only about 80% or more similar, 90% or more similar, 95% or more similar, 97% or more similar, 99% or more similar, or about 100% similar. Functional equivalency or conservation of biological function may be evaluated by methods for structural determination and bioassay.

The codons used may also be adapted for translation in a heterologous host by adopting the codon preferences of the host. This would accommodate the translational machinery of the heterologous host without a substantial change in chemical structure of the polypeptide.

Recombinant forms of protein C can be produced with a selected chemical structure (e.g., native, mutant, or polymorphic). As an illustration, a gene encoding human protein C is described in U.S. Pat. No. 4,775,624 and can be used to produce recombinant human protein C as described in U.S. Pat. No. 4,981,952. Human protein C can be recombinantly produced in tissue culture and activated as described in U.S. Pat. No. 6,037,322. Natural human protein C can be purified from plasma, activated, and assayed as described in U.S. Pat. No. 5,084,274. The nucleotide and amino acid sequence disclosed in these patents may be used as a reference for protein C.

The APC and/or protein C may also be glycosylated by methods well known in the art and which may comprise enzymatic and non-enzymatic means.

Suitable functional fragments of an APC may be produced by cleaving purified natural APC or recombinant APC with well known proteases such as trypsin and the like, or more preferably, by recombinant DNA techniques or peptide/polypeptide synthesis. Such functional fragments may be identified by generating candidate fragments and assessing biological activity by, for example, assaying for activation of MMP-2, promotion of repair of a wounded endothelial monolayer and/or angiogenesis in chicken embryo chorioalantoic membrane (CAM) in a manner similar to that described in the examples provided herein. Preferably, functional fragments will be of 5 to 100 amino acids in length, more preferably, of 10 to 30 amino acids in length. The functional fragments may be linear or circularised and may include modifications of the amino acid sequence of the native APC sequence from whence they are derived (eg amino acid substitutions, deletions, and additions of heterologous amino acid sequences). The functional fragments may also be glycosylated by methods well known in the art and which may comprise enzymatic and non-enzymatic means.

Suitable APC mimetic compounds (ie compounds which mimic the function of APC) may be designed using any of the methods well known in the art for designing mimetics of peptides based upon peptide sequences in the absence of secondary and tertiary structural information. For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity).

Alternatively, the mimetic compounds may be so-called peptoids (ie non-peptides) which include modification of the peptide backbone (ie by introducing amide bond surrogates by, for example, replacing the nitrogen atoms in the backbone with carbon atoms), or include N-substituted glycine residues, one or more D-amino acids (in place of L-amino acid(s)) and/or one or more α-amino acids (in place of β-amino acids or γ-amino acids). Further mimetic compound alternatives include "retro-inverso peptides" where the peptide bonds are reversed and D-amino acids assembled in reverse order to the order of the L-amino acids in the peptide sequence upon which they are based, and other non-peptide frameworks such as steroids, saccharides, benzazepinel,3,4-trisubstituted pyrrolidinone, pyridones and pyridopyrazines. Suitable mimetic compounds may also be designed/identified by structural modelling/determination, by screening of natural products, the production of phage display libraries, minimised proteins, SELEX (Aptamer) selection, combinatorial libraries and focused combinatorial libraries, virtual screening/database searching, and rational drug design techniques well known in the art.

Suitable pharmaceutical compositions of APC comprise the APC and a pharmaceutically-acceptable carrier. See, e.g., U.S. Pat. Nos. 6,395,270 and 6,159,468 and PCT applications WO 98/48818, WO 01/56532 and WO 01/72328. An APC-containing composition may generally be one that is a stable lyophilized product of high purity comprising a bulking agent (such as sucrose, mannitol, trehalose, and raffinose), a salt (such as sodium chloride and potassium chloride), a buffer (such as sodium citrate, Tris-acetate, and sodium phosphate), and APC. For example, a stable lyophilized composition may comprise a weight ratio of about 1 part APC, between about 7-8 parts salt, and between about 5-7 parts bulking agent. An example of such a stable lyophilized composition is: 5.0 mg APC, 30 mg sucrose, 38 mg NaCl, and 7.56 mg citrate, pH 6.0, per vial.

The various recombinant and synthetic forms of APC and APC analogues can be tested for use in the treatment of a pathologic scar by screening for the relevant efficacy in an established animal model, examples of which include a nude mouse model of hypertrophic scar discussed in Momtazi et al. 2013 supra.

F.1 Topically Administered Formulation

In one particularly preferred embodiment, the APC or APC-3K3A (SEQ ID NO: 1) is provided in the form of a composition or formulation that is adapted for topical administration to a relevant site of tissue injury, according to a method described under Sections D or E above. Examples of such formulations include those that can be applied directly to the relevant surface enabling local administration of the APC or APC-3K3A (SEQ ID NO: 1) to the relevant site. These formulations include gels, oils, sprays, roll on formulations, ointments, lotions, foams and the like. In one embodiment, the APC or APC-3K3A (SEQ ID NO: 1) is provided in the form of a methyl-cellulose gel and may contained stabilisers such as carbohydrates and salts.

Skin ointment may be a combination of organic, health, beauty or medicinal ingredients, usually in a petroleum oil base. This gives skin ointment a thicker, less water-soluble formula that stays on the surface of the body longer so that the ingredients can work more effectively to treat a wide variety of problems. There are many natural and organic skin ointments which can be ordered from companies (such as Therapex).

Clobetasol propionate (CP) foam (0.05%) may also be used. This is an emulsion aerosol foam that has been used for the treatment of inflammatory and pruritic manifestations of corticosteroid-responsive dermatoses in the United States and for inflammatory and pruritic manifestations of moderate to severe atopic dermatitis in Canada (Olux-E (clobetasol propionate) foam, 0.05% Stiefel Laboratories Inc, Research Triangle Park, N.C. (2011).

Where the formulation is a gel, it may contain APC or APC-3K3A (SEQ ID NO: 1) in an amount of 100-5000 µg/g gel.

F.2 Injectable Formulation

One formulation of APC is the product sold by Eli Lilly and Co., Indianapolis, Ind., under the trademark Xigris™. Xigris™ is supplied as a sterile, lyophilized powder for intravenous infusion. The 5 mg vials of Xigris™ contain 5.3 mg/vial of human recombinant APC, 31.8 mg/vial sucrose, 40.3 mg/vial NaCl, and 10.9 mg/vial sodium citrate, and the 20 mg vials of Xigris™ contain 20.8 mg/vial of human recombinant APC, 124.9 mg/vial sucrose, 158.1 mg/vial NaCl, and 42.9 mg/vial sodium citrate. The vials are reconstituted with Sterile Water for Injection, USP, to give a concentration of about 2 mg/ml APC, and this diluted APC is then added to 0.9% Sodium Chloride Injection to give a concentration of from about 100 to about 5000 µg/ml APC for administration to a patient. This is a particularly preferred formulation for administration of APC by subcutaneous injection techniques as described under Sections D or E above.

Whether administered topically or by sub cutaneous injection, in certain embodiments, the relevant formulation may contain protein C as an alternative to, or in addition to APC. For instance, an effective amount of protein C can be administered which will be activated in vivo by the endogenous protein C pathway to produce APC. See, e.g., U.S. Pat. No. 5,151,268 and PCT application WO 93/09807. As noted above, protein C can be purified from plasma or can be made by recombinant DNA techniques. See, e.g., U.S. Pat. Nos. 4,959,318, 4,981,952, 5,093,117, 5,151,268, 5,571,786, 6,156,734, 6,268,344, and 6,395,270. Suitable pharmaceutical compositions comprising protein C are known (see, e.g., U.S. Pat. Nos. 5,151,268 and 5,571,786).

Endogenous production of APC can also be increased by administering an amount of an agent that increases the synthesis of protein C in the animal. See, e.g., PCT application WO 93/09807. Suitable agents include anabolic steroids (e.g., danazolol). See, e.g., PCT application WO 93/09807.

In certain embodiments, endogenous production of APC can be increased by administering an amount of a protein C activator effective to cause the production of APC in vivo from endogenously synthesized protein C and/or from co-administered protein C. See, e.g., PCT application WO 93/09807. A protein C activator is any compound that causes or increases the generation of APC. Suitable protein C activators include thrombin, α-thrombin, active site acylated thrombin, thrombin analogs and mutants (e.g., thrombin E192Q and thrombin K52E), soluble thrombin-thrombomodulin complexes, agents that would prevent clearance or decay of thrombin-thrombomodulin complexes, agents that enhance the synthesis or delay the clearance of thrombomodulin, a venom (such as Protac or Russel Viper venom), factor Xa, plasmin, trypsin, and any other venom, enzyme or compound capable of causing or increasing the generation of APC from protein C. See, e.g., PCT application WO 93/09807. Preferred protein C activators are thrombin and active site acylated thrombin.

In some embodiments, APC may be administered with another agent for controlling one or more or inflammation, cell proliferation and apoptosis. One particularly preferred agent is an anti-IL-17 antibody, in particular Ixekizumab, which showed significant improvements in skin disease severity scores compared with placebo in a Phase II Study in Patients With Chronic Plaque Psoriasis (NEJM, 2012). Other examples of agents for controlling inflammation include TNF-α inhibitors and anti-inflammatory cytokines and biopharmaceuticals.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

Figure 1:
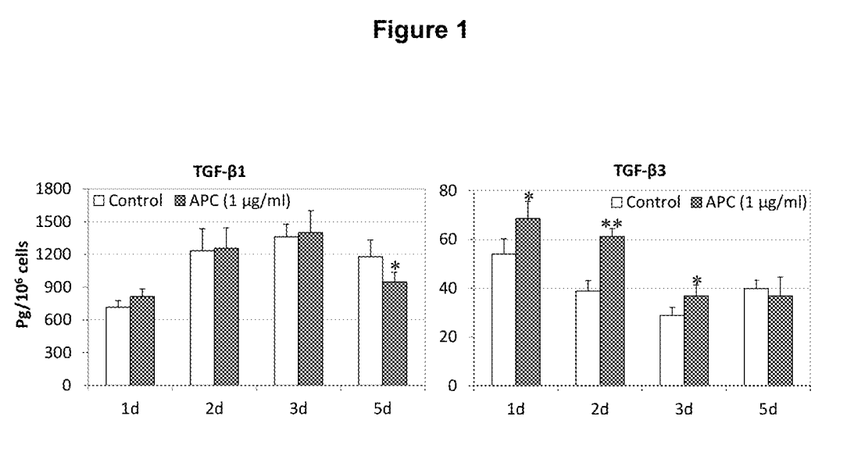
FIG. 1: The production of TGF-β1 and TGF-β3 by APC treated human keratinocytes.

Human neonatal foreskin keratinocytes were cultured to confluence in 24-well plates. The monolayers were treated with 1 µg/ml recombinant APC. Culture supernatants were collected at days 1, 2, 3 and 5 after treatment. TGF-β1 and TGF-β3 in supernatants were detected by enzyme-linked immunosorbent assay.

Example 2

Figure 2:
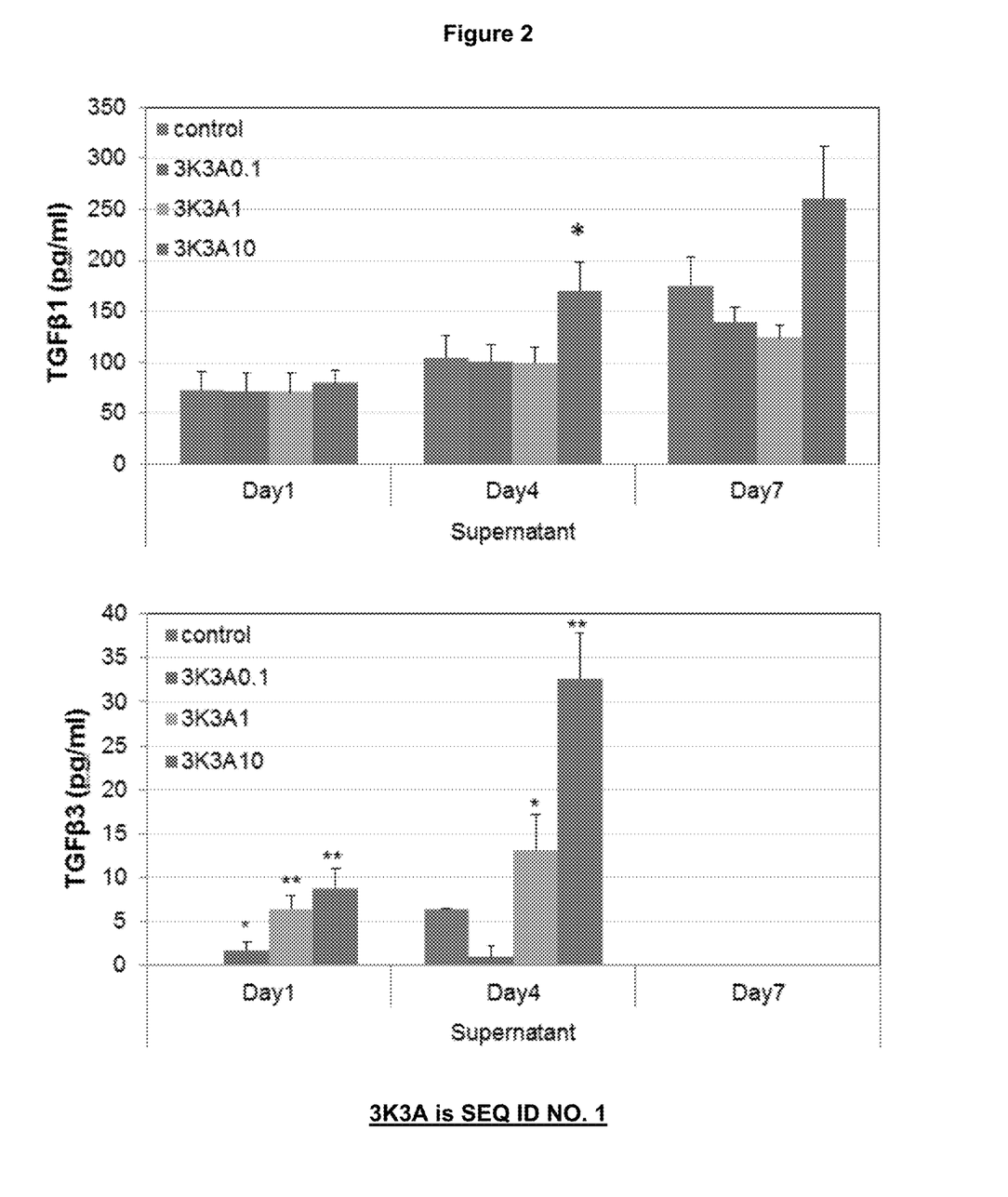
FIG. 2: The production of TGF-β1 and TGF-β3 by APC-3K3A (SEQ ID NO: 1) treated human fibroblasts.

Effect of 3K3A-APC (SEQ ID NO: 1) on Neonatal dermal fibroblasts. Cells were cultured 24-well plates to confluence and switched to serum free media. Cells then were treated with 3K3A-APC (SEQ ID NO: 1) for 1, 4 or 7 days. Culture supernatants were collected at designated time points. TGFβ1 and 3 were measured by ELISA. Data represent the means of 2 experiments. *$P<0.05$, **$P<0.01$ when compared to control at the same time point.

The invention claimed is:

1. A method for minimizing or reducing the appearance of a pathologic scar in an individual including the steps of:
   providing the individual having the pathologic scar;
   contacting the pathologic scar with an activated protein C (APC) analogue, wherein the APC analogue consists of 3K3A-APC;
   thereby minimizing or reducing the appearance of the pathologic scar in the individual.

2. The method of claim 1 wherein the scar is a hypertrophic scar.

3. The method of claim 1 wherein the APC analogue is provided topically or in a form of an injectable composition for use in the method.

4. The method of claim 1 wherein the APC analogue is provided in an amount of from 0.1 μg to 5000 μg of the APC analogue per $cm^2$ of a region of skin to which the APC analogue is applied.

5. The method of claim 1 wherein the APC analogue is provided at least once per day.

6. The method of claim 1 wherein the APC is provided for a period of about 4 to 20 weeks.

7. The method of claim 1 wherein the APC analogue is provided in an amount of from 1 μg to 2000 μg of APC analogue per $cm^2$ of a region of skin to which the APC analogue is applied.

8. The method of claim 1, wherein the APC analogue is provided in an amount of from 10 μg to 1000 μg of the APC analogue per $cm^2$ of a region of skin to which the APC analogue is applied.

9. The method of claim 1, wherein the APC analogue is provided in an amount of from 10 μg to 500 μg of the APC analogue per $cm^2$ of a region of skin to which the APC analogue is applied.

* * * * *

SEQUENCE LISTING

<160> NUMBER OF SEQ ID NOS: 3

<210> SEQ ID NO 1
<211> LENGTH: 419
<212> TYPE: PRT
<213> ORGANISM: Artificial Sequence
<220> FEATURE:
<223> OTHER INFORMATION: Recombinant

<400> SEQUENCE: 1

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe

```
                355                 360                 365
His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 2
<211> LENGTH: 4
<212> TYPE: PRT
<213> ORGANISM: Artificial Sequence
<220> FEATURE:
<223> OTHER INFORMATION: RKRR

<400> SEQUENCE: 2

Arg Lys Arg Arg
1

<210> SEQ ID NO 3
<211> LENGTH: 4
<212> TYPE: PRT
<213> ORGANISM: Artificial Sequence
<220> FEATURE:
<223> OTHER INFORMATION: AAAA

<400> SEQUENCE: 3

Ala Ala Ala Ala
1
```